US006926003B2

(12) United States Patent
Seppälä

(10) Patent No.: US 6,926,003 B2
(45) Date of Patent: Aug. 9, 2005

(54) MULTIDOSE POWDER INHALER

(75) Inventor: Kari Seppälä, Helsinki (FI)

(73) Assignee: Orion Corporation, Espoo (FI)

( * ) Notice: Subject to any disclaimer, the term of this patent is extended or adjusted under 35 U.S.C. 154(b) by 0 days.

(21) Appl. No.: 10/148,595

(22) PCT Filed: Dec. 7, 2000

(86) PCT No.: PCT/FI00/01078

§ 371 (c)(1),
(2), (4) Date: Oct. 1, 2002

(87) PCT Pub. No.: WO01/41850

PCT Pub. Date: Jun. 4, 2001

(65) Prior Publication Data

US 2003/0136406 A1 Jul. 24, 2003

(30) Foreign Application Priority Data

Dec. 7, 1999 (FI) ............................................. 19992620

(51) Int. Cl.⁷ ........................................... A61M 15/00
(52) U.S. Cl. .............................. 128/203.15; 128/203.12
(58) Field of Search ...................... 128/203.15, 203.21, 128/203.12; 604/58

(56) References Cited

U.S. PATENT DOCUMENTS

| | | | | |
|---|---|---|---|---|
| 43,536 A | * | 7/1864 | Vergnes .................. | 128/203.15 |
| 137,093 A | * | 3/1873 | Pinchard ................. | 128/203.15 |
| 237,468 A | * | 2/1881 | Bell ........................... | 422/124 |
| 1,811,898 A | * | 6/1931 | Schur et al. ................. | 222/368 |
| 1,858,735 A | * | 5/1932 | Goodsell ..................... | 222/162 |
| 1,879,111 A | * | 9/1932 | Crandall ....................... | 111/74 |
| 2,381,454 A | * | 8/1945 | Huth ............................ | 141/59 |
| 2,573,918 A | * | 11/1951 | McCuiston ............. | 128/200.17 |
| 2,587,215 A | * | 2/1952 | Priestly .................. | 128/203.15 |
| 3,870,046 A | * | 3/1975 | Elliott ................... | 128/203.15 |
| 4,184,258 A | * | 1/1980 | Barrington et al. ........... | 433/88 |
| 4,200,099 A | * | 4/1980 | Guenzel et al. ......... | 128/203.15 |
| 4,307,734 A | * | 12/1981 | Blankenship ................ | 131/329 |
| 4,446,862 A | * | 5/1984 | Baum et al. ........... | 128/203.15 |
| 4,452,239 A | * | 6/1984 | Malem .................. | 128/200.17 |
| 4,524,769 A | * | 6/1985 | Wetterlin ............... | 128/203.15 |
| 4,534,345 A | * | 8/1985 | Wetterlin ............... | 128/203.15 |
| 4,668,218 A | * | 5/1987 | Virtanen ....................... | 604/58 |
| 4,805,811 A | * | 2/1989 | Wetterlin .................... | 222/337 |
| 4,907,583 A | * | 3/1990 | Wetterlin et al. ...... | 128/203.15 |
| 4,961,521 A | * | 10/1990 | Eckman .................... | 222/142.5 |
| 5,004,021 A | * | 4/1991 | Ulyanitsky et al. ............ | 141/67 |
| 5,113,855 A | * | 5/1992 | Newhouse ............. | 128/203.12 |
| 5,176,132 A | * | 1/1993 | Drought et al. ........ | 128/203.15 |
| 5,239,992 A | * | 8/1993 | Bougamont et al. ... | 128/203.15 |
| 5,295,479 A | * | 3/1994 | Lankinen ............... | 128/203.15 |
| 5,301,666 A | * | 4/1994 | Lerk et al. ............. | 128/203.15 |

(Continued)

FOREIGN PATENT DOCUMENTS

| | | |
|---|---|---|
| EP | 0 079 478 | 5/1983 |
| EP | 0 166 294 | 1/1986 |
| GB | 2 165 159 | 4/1986 |
| WO | WO 02/00771 | 1/1992 |
| WO | WO 92/09322 | 6/1992 |
| WO | WO 93/00123 | 1/1993 |

Primary Examiner—Aaron J. Lewis
(74) Attorney, Agent, or Firm—Finnegan, Henderson, Farabow, Garrett & Dunner, LLP

(57) ABSTRACT

A powder inhaler comprises a medicament container, a rotatable metering disc extending into the interior of the medicament container and an air channel through which air is drawn via a mouthpiece. The metering disc has one or more peripherally located dosing grooves extending axially through the metering disc. The dosing grooves are filled with a metered dose of the medicament while being inside the medicament container and are transferred to the air channel wherein the stream of inhaled air discharges the dose of the medicament directly from the dosing groove.

8 Claims, 6 Drawing Sheets

U.S. PATENT DOCUMENTS

| | | | |
|---|---|---|---|
| 5,320,714 A | * 6/1994 | Brendel | 128/203.15 |
| 5,349,947 A | * 9/1994 | Newhouse et al. | 128/203.21 |
| 5,351,683 A | * 10/1994 | Chiesi et al. | 128/203.12 |
| 5,429,122 A | * 7/1995 | Zanen et al. | 128/203.15 |
| 5,435,301 A | * 7/1995 | Herold et al. | 128/203.15 |
| 5,447,151 A | 9/1995 | Bruna et al. | |
| 5,542,411 A | * 8/1996 | Rex | 128/203.15 |
| 5,575,280 A | * 11/1996 | Gupte et al. | 128/203.15 |
| 5,582,162 A | * 12/1996 | Petersson | 128/203.15 |
| 5,634,900 A | * 6/1997 | Makino et al. | 604/58 |
| RE35,552 E | * 7/1997 | Lankinen | 128/203.12 |
| 5,678,538 A | * 10/1997 | Drought | 128/203.15 |
| 5,857,457 A | * 1/1999 | Hyppola | 128/203.15 |
| 5,996,577 A | * 12/1999 | Ohki et al. | 128/203.15 |
| 6,220,243 B1 | * 4/2001 | Schaeffer et al. | 128/203.15 |
| 6,332,461 B1 | * 12/2001 | Hyppola | 128/203.15 |
| 6,557,550 B1 | * 5/2003 | Clarke | 128/203.15 |

\* cited by examiner

MULTIDOSE POWDER INHALER

This application is a U.S. national stage filing of International Application No. PCT/FI00/01078, filed on Dec. 7, 2000. This application claims the benefit of priority under 35 U.S.C. § 119(a) to Finnish patent application Ser. No. 19992620, filed on Dec. 7, 1999.

BACKGROUND OF THE INVENTION

The present invention relates to a device for dispensing of a powdered drug preparation by inhalation. The device is in particular a multiple-dose device without propellant gas, equipped with a metering means, which dispenses doses from a powder container. The device of the invention is useful, for example, in the treatment of asthma.

The administering of a powdered drug preparation by inhalation from an inhaler is known. Multidose type powder inhalers comprising a drug container and a metering member for measuring and dispensing a unit dose are also known, for example from patent publications GB 2165159, EP 79478, and EP 166294. In these devices, a series of dosing recesses are notched into the surface of a cylindrical metering member, and the said member is disposed in a chamber of precisely the same shape. When the metering member is rotated, the dosing recesses in turn will move first to a position in alignment with the powder container for being filled and thereafter to a position in alignment with the inhalation channel, whereupon an unit dose will fall by gravity from the dosing recess into the inhalation channel. Thereafter the dose of medicament is inhaled from the inhalation channel. These devices have the drawback that they make overdosing of the medicament possible by allowing the dispensing of a plurality of doses in succession into the inhalation channel, whereby a multiple dose may be drawn by one inhalation.

Attempts have been made to solve the above-mentioned problem by using dispensing systems in which the dosing recess will not be emptied into the inhalation channel by gravity but, instead, the dose of medicament is inhaled directly from the dosing recess, such recesses having been notched into the surface of a metering member having the shape of a cylinder, a cone or a truncated cone, as disclosed in patent publications WO 92/00771 and WO 92/09322. Also in these devices, a metering member having the shape of a cylinder, a cone or a truncated cone is disposed in a chamber having precisely the same shape. When the metering member is rotated, the dosing recesses will move first to a position in alignment with the flow container for filling, and then to the inhalation channel, which is shaped so that the dosing recess will be emptied under the effect of the air flow being inhaled, and thereafter, having rotated through a full 360°, back to a position in alignment with the flow container. Since the metering member is, for purposes of metering precision, disposed within a chamber of the same shape, and since it has to be rotated through 360°, the metering member may be prone to jamming as powder falls onto the surfaces of the device.

The above devices have a further drawback of dosing inaccuracy. The dosing recess of the above devices is filled with powder when the dosing recess is in alignment with the bottom aperture of the container the powder flowing through the aperture under the effect of gravity. If the aperture is temporarily blocked, e.g. by lumps or by arching of the powder in the container, the dosing recess will be filled incompletely or will remain empty.

SUMMARY OF THE INVENTION

The object of the present invention is to construct a multidose powder inhaler which avoids the above mentioned disadvantages. The device of the invention has good metering accuracy, it is not susceptible to jamming and provides complete discharge of the powdered dose into the breathing air even if used by a patient having reduced inhalation capacity. Furthermore, the device is simple and can be operated with one hand.

This is achieved by providing a device for dispensing powdered medicament by inhalation, comprising a medicament container for receiving a plurality of medicament doses, the wall of said container having an elongate slot into which a rotatable metering disc is secured by means of a disc axis the metering disc extending into the interior of the medicament container;

an air channel through which air is drawn via a mouthpiece;

in the metering disc one or more peripherally located dosing grooves, which extend axially through the metering disc, for receiving a metered dose of the medicament while being inside the medicament container and for transferring the metered dose of the medicament from the medicament container to the air channel;

the air channel comprising a conduit across which the metering disc is slidably fitted such that for inhalation the dosing groove containing a metered dose of the medicament is brought in register with said conduit; and the metering disc being in sliding contact with a supporting wall extending to the level of the conduit so as to prevent falling of the metered dose of the medicament out of the dosing groove as it is transferred from the medicament container to the air channel, the stream of inhaled air discharging the dose of the medicament directly from the dosing groove.

Rather than having the metering disc positioned below the medicament container, the device is constructed such that the metering disc itself enters the container. As the metering disc is rotated, the dosing grooves travel inside the medicament container and are effectively filled with the powdered medicament. At the same time the metering disc agitates the powder in the container and thus reduces arching of the powder and lump formation.

As the metering disc is rotated further, the dosing groove filled with a dose of the medicament is transferred from the container to the air channel. The dosing groove is brought in register with the air channel to be inhaled by the patient. The air channel suitably comprises a conduit across which the metering disc is slidably fitted. The longitudinal axis of the conduit and the rotation axis of the metering disc are preferably substantially parallel. In this way substantially all inhaled air may be conducted through the dosing groove, whereby the medicament is completely discharged into the air stream. As the powder is discharged directly from the dosing groove, the possibility of overdosing by inhaling multiple doses is avoided. The cross-sectional shape of the conduit may vary a circular cross-sectional shape being preferred. Thus the conduit is suitably in the form of a cylindrical element.

In order to prevent falling of the metered dose of the medicament out of the dosing groove as it is transferred from the medicament container to the air channel, the device comprises a supporting wall element, which the surface of the metering disc is in sliding contact with. The supporting wall is preferably in the form of an annular wall segment, the surface of which suitably completes the substantially circular cross-section of the dosing groove. Accordingly, in a preferred embodiment the dosing groove forms together with a cylindrical air conduit a substantially continuous tube, when they are in register with each other. Even though the dosing groove has preferably a rounded or substantially circular cross-section, other cross-sectional forms, such as (but not limited to) rectangular, triangular, square, arcuate or shapes formed by combinations of straight and arcuate line segments, can also be used.

The metering disc is secured into the elongate slot of the container wall by means of a disc axis so that the metering disc extends into the interior of the medicament container. Preferably the disc axis is arranged so as to cross the medicament container. Thereby the metering disc can be provided with one or more agitation members for more effective powder agitation. The agitation members are suitably in the form of pins extending from the flat sides of the metering disc parallel to its axis.

The device of the invention preferably comprises means for stepwise rotation of the metering disc. The means for stepwise rotation ensures that the filled dosing groove is brought closely in register with the air channel each time the patient actuates the inhaler. The stepwise rotation of the metering disc can be implemented in number of ways. For example, the device may have a depressible cover to which a driving member for the rotatable metering disc is locked. The driving member may be secured for engagement with e.g. a ratchet mechanism or a like in a manner known to one skilled in the art, such that the rotation of the metering member can only be accomplished stepwise corresponding to the peripheral distance between the dosing grooves, and the rotation is only possible in one direction. The driving member may be arranged, for example, to engage with the dosing grooves causing the metering disc rotate one step each time the cover is depressed. However, alternative ways of achieving stepwise rotation of the metering disc are imaginable to one skilled in the art.

DETAILED DESCRIPTION OF THE INVENTION

The device of the invention is further illustrated below by way of examples with reference to FIGS. 1 to 12, wherein the inhaler device and its parts are depicted as transparent.

Figure 2:
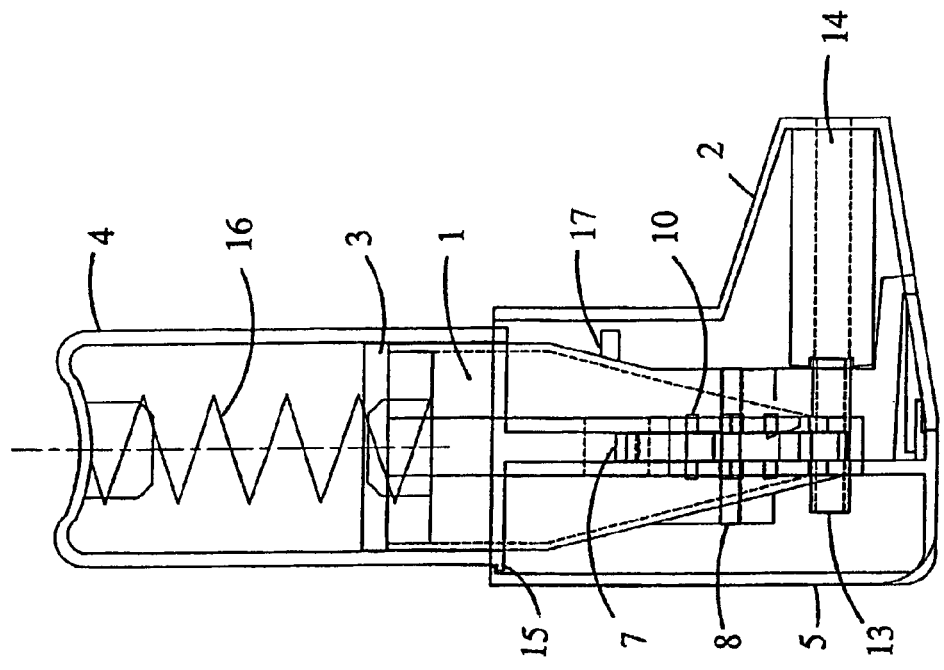
FIG. 2 is a side view of the inhaler device of FIG. 1.
Figure 1:
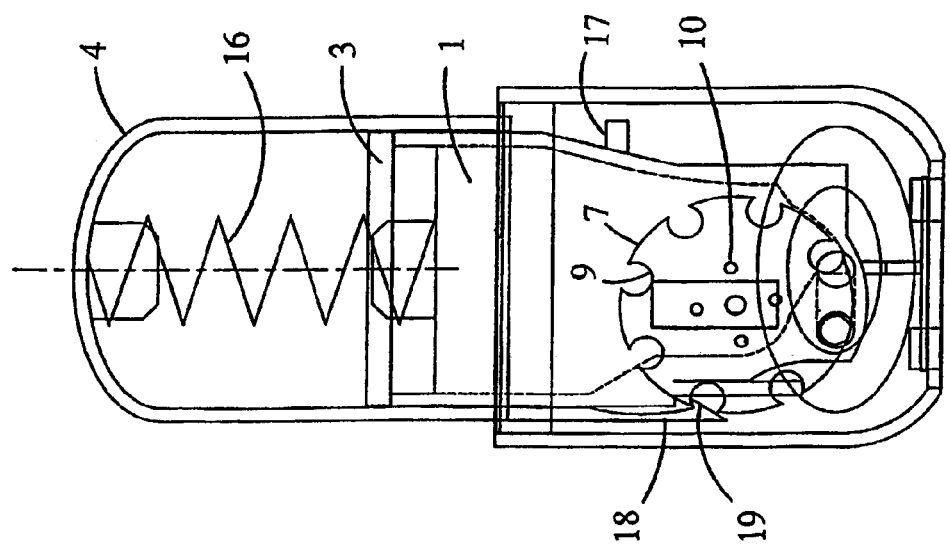
FIG. 1 is a front view of the inhaler device.

FIGS. 1 and 2 show a multidose powder inhaler with medicament container (1) for a certain supply of powdered medicament and a mouth piece (2). Normally, the container has a supply of medicament for e.g. 200 doses. The container (1) has a square cross-section and a substantially conical end portion. A lid (3) closes the upper edge of the medicament container. The cover (4) is adapted to cover the medicament container (1) and the lid (3). The container is moulded together with the rear wall (5) of the device. This can be seen more clearly in FIGS. 3 and 4 showing the container body of the inhaler device.

The wall of the container (1) has an elongate slot (6) into which a vertically positioned metering disc (7) is rotatably secured by means of a disc axis (8) crossing the medicament container (1). Thereby the entire height of the metering disc (7) enters the container (1). The metering disc (7) has several dosing grooves (9) located on the peripheral surface of the metering disc (7) and extending axially through the metering disc (7). The elongate slot (6), which is more clearly shown in FIG. 4, extends vertically along one side of the container (1). The dimensions of the elongate slot (6) correspond exactly with the shape of the metering disc (7) such that the metering disc (7) is in sliding contact with the sides of the slot (6) thereby preventing the flow of powder through the slot (6). The disc axis (8) is pushed through the metering disc (7) and through the guiding holes in the walls of the container (I) such that the disc axis (8) crosses the container (1). Thus the metering disc (7) extends into the interior of the container (1) such that some dosing grooves (9) are inside and others outside the container (1). When the metering disc (7) is rotated clockwise around the axis (8) each dosing groove (9) is transferred from outside to inside the container (1) and vice versa. The metering disc (7) is further equipped with four agitation members (10) in the form of pins extending from the flat sides of the metering disc (7) parallel to its axis (8). The agitation members (10) are designed to effectively agitate the powdered medicament in the container as the metering disc (7) is rotated. Inside the container (1) the flat surfaces of the metering disc (7) are generally offset from the conical walls of the container (1). Thereby the powder can freely flow towards the tapered bottom of the container (1) in the space formed between the metering disc (7) and the conical walls of the container (1).

Figure 4:
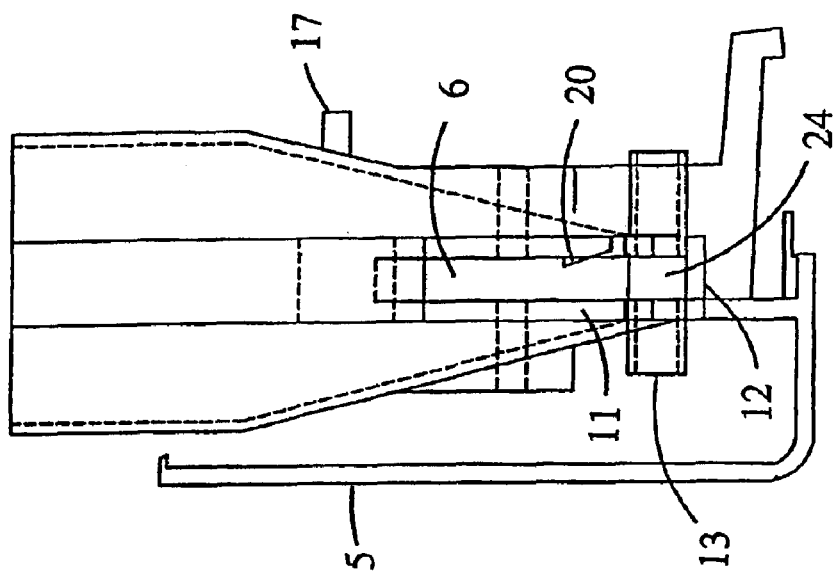
FIG. 4 is a side view of the container body of the device FIG. 1.
Figure 3:
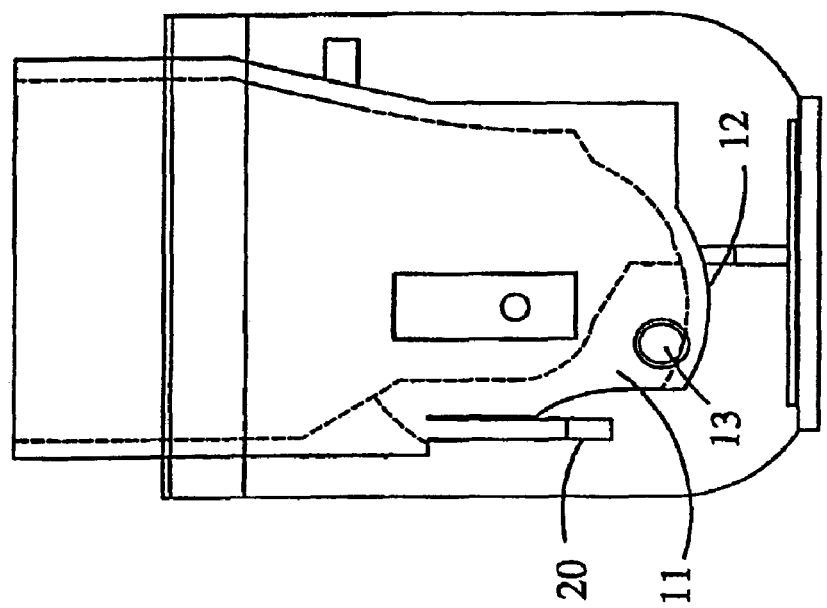
FIG. 3 is a front view of the container body of the device of FIG. 1.

Referring now to FIGS. 3 and 4, the portion of the metering disc (7) that remains outside the container is partially covered by guide walls (11) which the metering disc (7) is in sliding contact with. The guide walls (11) are moulded together with the medicament container (1). The guide walls (11) comprise an annular wall segment (12) which prevents the falling of metered dose of the medicament out of the dosing groove (9) while being transferred from the medicament container (1). The surface of the annular wall segment (12) completes the substantially circular cross section of the dosing groove (9).

The air channel comprises, in the vicinity of the metering disc (7), a conduit in the form of an open cylindrical element (13), best shown in FIG. 4, projecting from the vertical guide walls (11). The cylindrical element (13) is provided with an opening (24) for receiving a peripheral portion of the metering disc (7) the longitudinal axis of the cylindrical element (13) and the rotation axis of the metering disc being parallel. When the metering disc (7) is rotated, it slides across the conduit formed by the cylindrical element (13). The cylindrical element (13), which have a diameter corresponding to the diameter of the dosing groove (9) is positioned at the level of the annular wall segment (12) so that the dosing groove (9) can be brought in register with the cylindrical element (13). When the dosing groove (9) is in register with the cylindrical element (13), the dosing groove (9) and the cylindrical element (13) form together a continuous tube-like air channel such that substantially all inhaled air is conducted through the dosing groove (9). If desired, the cylindrical element (13) can be led, offset from the mouthpiece, to the rear wall (5), which can be provided with an air intake. Such embodiment would ensure that possible remnants of powder left on the inner surfaces of the device are not discharged into the inhaled air.

Figure 6:
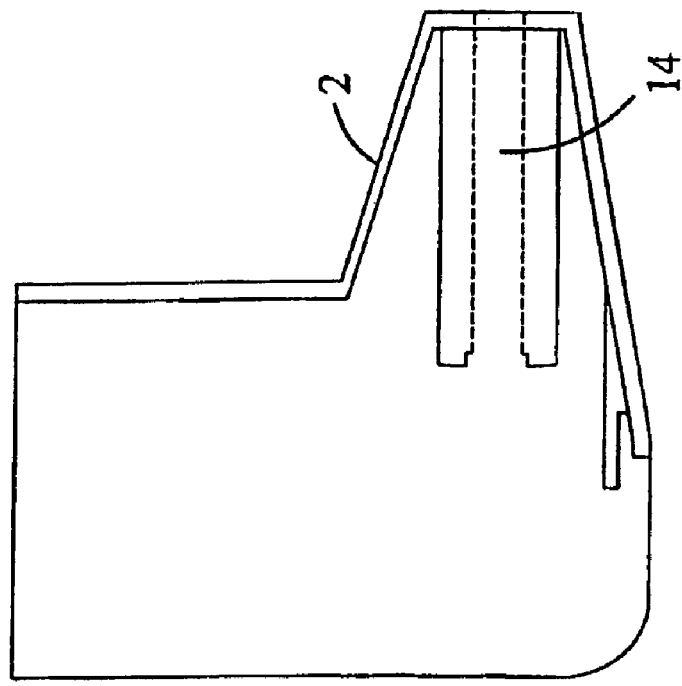
FIG. 6 is a side view of the mouthpiece of the device of FIG. 1.
Figure 5:
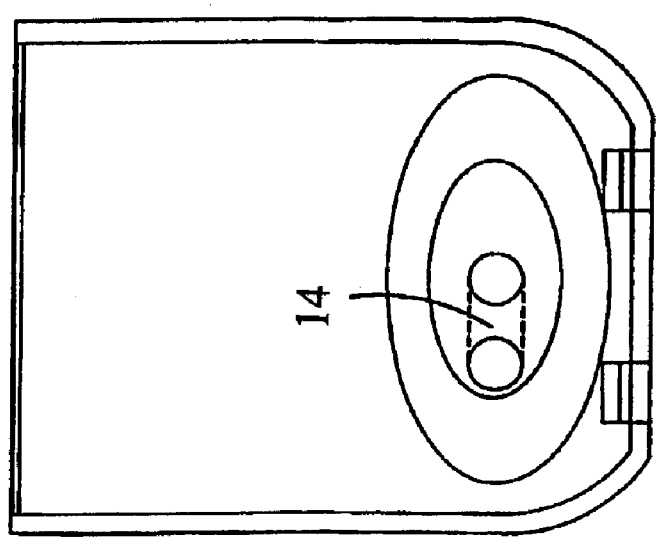
FIG. 5 is a front view of the mouthpiece of the device of FIG. 1.

The mouthpiece (2) is shown separately in FIGS. 5 and 6. The cylindrical element (13) is connected to an air passage (14) moulded inside the mouthpiece (2) by snap-fitting the mouthpiece (2) to the rear wall (5). Thus, when a dosing groove (9) containing a dose of medicament is in register with the cylindrical element (13), substantially all air inhaled by a patient through the mouthpiece (2) is conducted through the filled dosing groove (9).

Turning again to FIG. 1, the device has a depressible cover (4) serving as an actuating means of the device. The depressible cover (4) is attached between the rear wall (5) and the mouthpiece (2) by snapfastening means e.g. such as a peripheral lip (15) which puts an upward limit on the movement of the cover (4). The cover (4) is urged upwards by a spring (16) bearing firstly against the cover (4) and secondly against the lid (3).

The downward limit on the movement of the cover (4) is put by the projection (17) of the container (1). The cover (4) is provided with a driving member (18) for the stepwise rotation of the metering disc (7). The lower end of the driving member has a tooth-like projection (19) for engagement with the edge of a dosing groove (9) of the metering disc (7).

Figure 8:
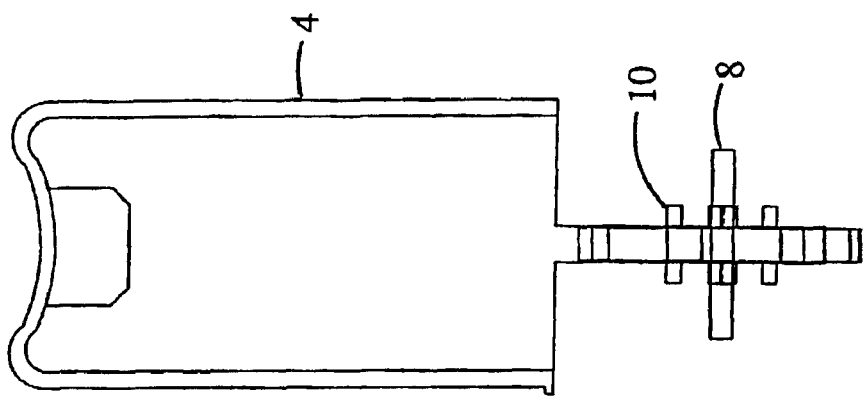
FIG. 8 is a side view of the metering disc, the cover and the driving member of FIG. 7.
Figure 7:
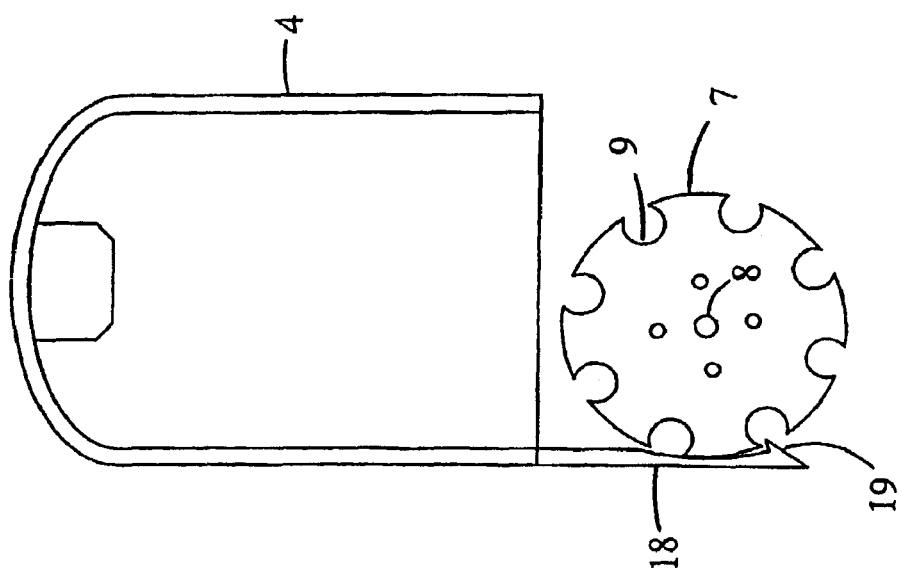
FIG. 7 is a schematic front view of the metering disc, the cover and the driving member of the device when the cover is in the depressed position.

The device is actuated by depressing the cover, whereby the driving member (18), having some flexibility in the direction of the side wall of the device, moves down until the tooth-like projection (19) is engaged with a dosing groove (9). Reference is made to FIGS. 7 and 8, which show schematically the cover (4) and the metering disc (7) in a position where the cover (4) has been depressed. The detent nose (20), more clearly shown in FIGS. 3 and 4, extending from the guide wall (11) also engages into a dosing groove (9) such that analogue to a ratchet rotation is only possible to one direction.

When the cover (4) is released, the cover and the driving member are urged upwards by the action of the spring (16). Thereby the tooth-like projection (19) of the driving member (18) causes the metering disc (7) rotate so that rotation can only be accomplished stepwise corresponding to the peripheral distance between the dosing grooves (9). The cylindrical element (13) forming the air channel and the detent nose (20) are positioned such that the driving member (18) automatically aligns one dosing groove (9) with the cylindrical element (13) forming the air channel.

Figure 10:
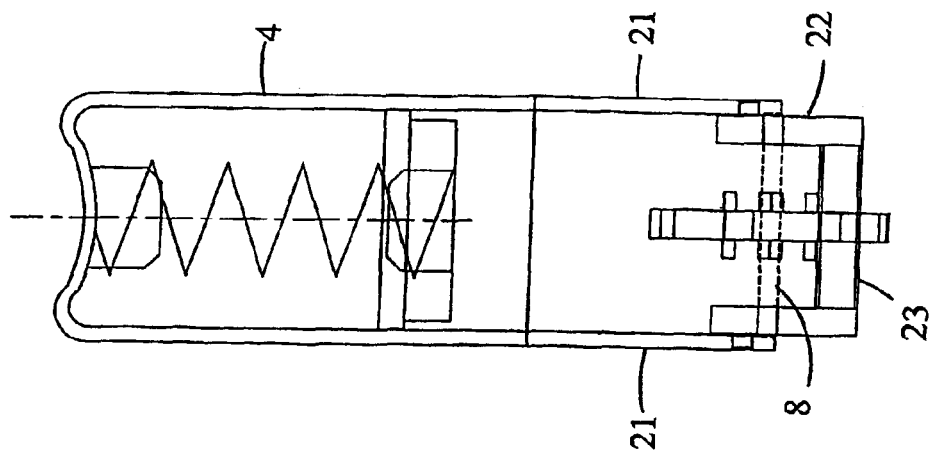
FIG. 10 is a side view of the metering disc, the cover and the driving member of FIG. 9.
Figure 9:
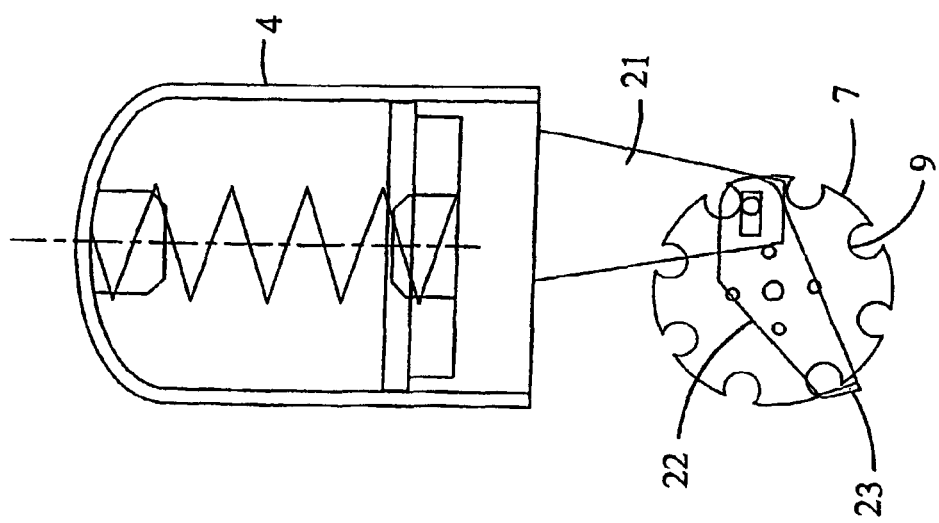
FIG. 9 is a schematic front view of an another embodiment of the metering disc, the cover and the driving member of the device when the cover is in the rest position.
Figure 12:
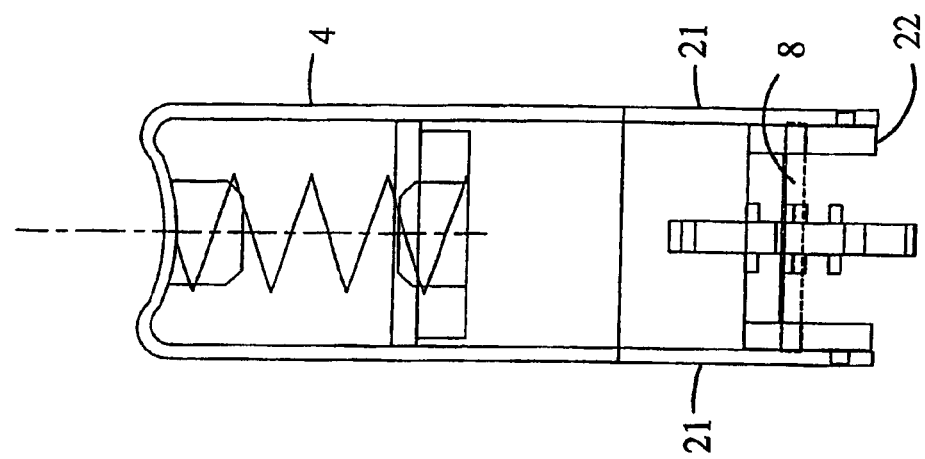
FIG. 12 is a side view of the metering disc, the cover and the driving member of FIG. 11.
Figure 11:
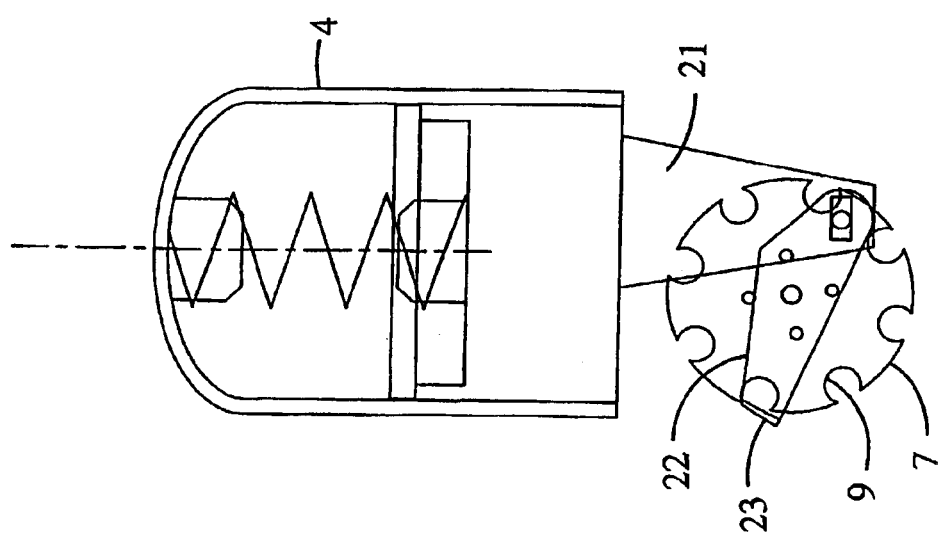
FIG. 11 is a schematic front view of the metering disc, the cover and the driving member of FIG. 9 in the depressed position.

An alternative way of implementing the stepwise rotation of the metering disc (7) is shown in FIGS. 9 and 10. The driving member consists of two parallel arms (21) projecting downwards from the opposite sides of the depressible cover (4). A lever member (22) is mounted firstly to the axis (8) of the metering disc (7) and secondly between the arms (21). The lever member (22) has an engagement portion (23) for the engagement with the dosing grooves (9) of the metering disc (7). When the cover (4) is depressed, as shown in FIGS. 11 and 12, until its downwards movement is stopped by the projection (17), the arms (21) cause pivoting of the lever member (22) whereby the engagement portion (23) of the lever member (22) causes the metering disc (7) to rotate.

The movement of the arms (21) is suitably adjusted such that the rotation corresponds to the peripheral distance between the dosing grooves (9). Again, also the detent nose (20), more clearly shown in FIGS. 3 and 4, engages into a dosing groove (9) such that analogue to a ratchet the stepwise rotation is only possible to one direction.

Other modifications and variations can be made to the disclosed embodiments without departing from the subject of the invention as defined in the following claims. For example, a counter could be mounted to the inhaler to count the number of pressing of the actuating means. It is considered to be routine for one skilled in the art to make such modifications to the device of the invention.

What is claimed is:

1. A device for dispensing powdered medicament by inhalation, comprising
    a medicament container for receiving a plurality of medicament doses, the wall of said container having an elongate slot into which a rotatable metering disc is secured by a disc axis, the metering disc extending into the interior of the medicament container;
    an air channel through which air can be drawn via a mouthpiece;
    in the metering disc one or more peripherally located dosing grooves, which extend axially through the metering disc, capable of receiving a metered dose of medicament while being inside the medicament container and capable of transferring a metered dose of medicament from the medicament container to the air channel;
    the air channel comprising a conduit across which the metering disc is slidably fitted such that for inhalation a dosing groove containing a metered dose of medicament can be brought in register with said conduit; and
    the metering disc being in sliding contact with a supporting wall extending to the level of the conduit so as to prevent falling of a metered dose of med icament out of the dosing groove throughout its transfer from the medicament container to the air channel, whereby a stream of inhaled air discharges a dose of medicament directly from the dosing groove.

2. A device of claim 1, wherein the supporting wall is in a form of an annular wall segment extending to the bottom of the conduit.

3. A device of claim 1, wherein substantially all inhaled air can be conducted through the dosing groove.

4. A device of claim 1, wherein the disc axis crosses the medicament container.

5. A device of claim 4, wherein the metering disc is provided with one or more agitation members.

6. A device of claim 5, wherein the agitation members are in the form of pins extending from the flat sides of the metering disc parallel to its axis.

7. A device of claim 1, comprising means for stepwise rotation of the metering disc.

8. A device of claim 7, comprising a depressible cover to which a driving member for rotating the metering disc is locked.

* * * * *